United States Patent [19]

Crowley

[11] 4,299,568
[45] Nov. 10, 1981

[54] ORTHODONTIC APPLIANCE

[76] Inventor: John A. Crowley, 4743 Bradley Blvd., Chevy Chase, Md. 20015

[21] Appl. No.: 159,451

[22] Filed: Jun. 13, 1980

[51] Int. Cl.³ .............................................. A61C 7/00
[52] U.S. Cl. ......................................................... 433/6
[58] Field of Search ....................................... 433/6, 7

[56] References Cited

U.S. PATENT DOCUMENTS

| | | | |
|---|---|---|---|
| 1,504,942 | 8/1924 | Comegys | 433/7 |
| 3,967,379 | 7/1976 | Bergersen | 433/6 |
| 3,994,068 | 11/1976 | Goshgarian | 32/14 E |

OTHER PUBLICATIONS

Great Lakes, Orthodontic Laboratories Inc., 1550 Hertel Ave., Buffalo, N. Y., 14216, May 7, 1979.
The New Linde Auto-Active Orthodontic Appliances, 145 West Forty-First St., N. Y., N. Y., May 24, 1939, p. 8.

Primary Examiner—Robert Peshock
Attorney, Agent, or Firm—Sixbey, Friedman & Leedom

[57] ABSTRACT

A dual function orthodontic appliance which permits the orthodontist a wide variety of treatment options in repositioning the teeth to achieve the most orthodontically desirable positions and in maintaining the repositioned teeth in the desired positions is provided. The orthodontic appliance of the present invention includes a palatal overlay molded to conform to the contours of the patient's hard plate and to fit securely against the gingival edge of the lingual surface of the teeth, a pair of posteriorly positioned opposed clasps, and a pair of opposed, spaced retaining and positioning wires which cross over the anterior teeth for a distance necessary to achieve the desired positioning or retaining effect. The orthodontic appliance of the present invention may be adapted to treat the lower teeth by providing in place of the palatal overlay a gingival overlay molded to conform to the periodontal structures on the lingual side of the lower teeth. An additional embodiment provided includes a single continuous substantially horizontal retaining wire having at least one preferably centrally positioned inverted U-shaped adjustment loop which may be clipped to convert the single wire appliance of this embodiment to the more versatile double wire configuration appliance.

18 Claims, 10 Drawing Figures

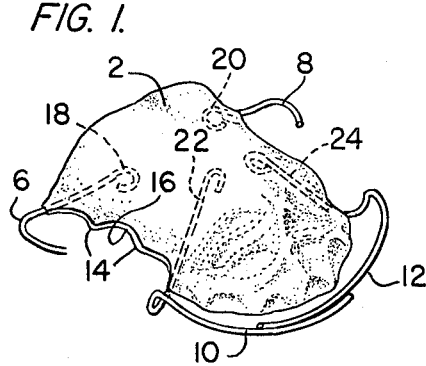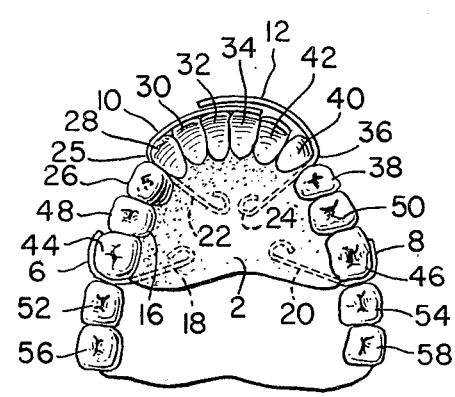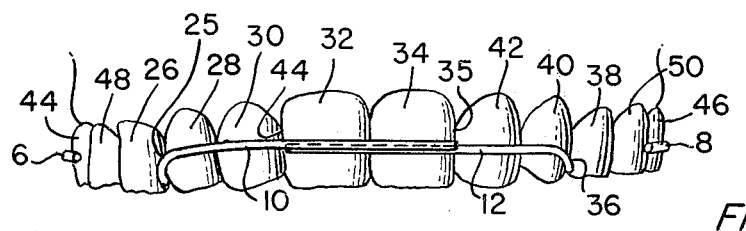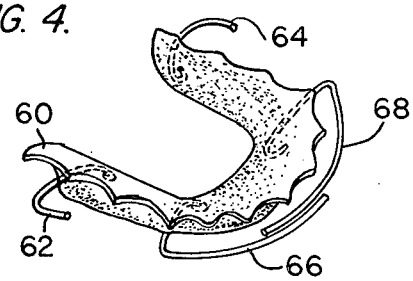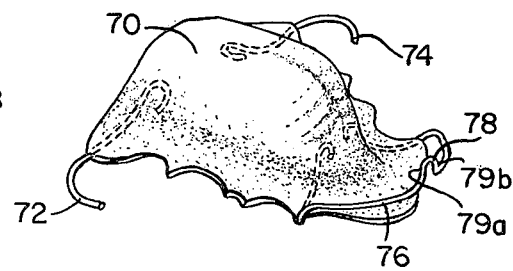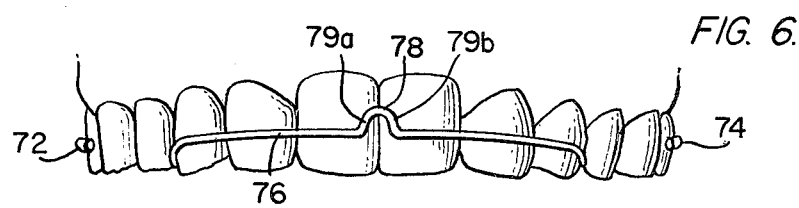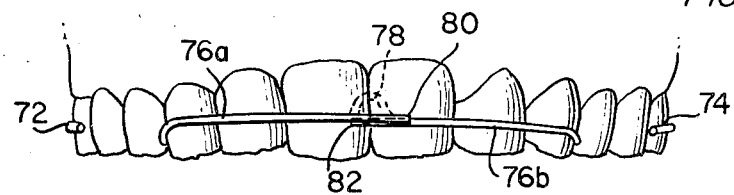

ORTHODONTIC APPLIANCE

TECHNICAL FIELD

The present invention relates generally to orthodontic appliances for positioning the teeth and maintaining them in orthodontically correct positions and, in particular, to a retainer-like appliance including a pair of dual function labial wires which can be applied either to move the teeth into orthodontically correct positions or to stabilize the teeth in previously achieved correct positions.

BACKGROUND ART

The traditional approach to a course of orthodontic treatment in a patient whose teeth require repositioning has been to achieve the necessary movement of the teeth by the application of orthodontic appliances generally known as braces. These orthodontic appliances are typically formed of a series of metal bands which encircle the teeth and are interconnected by wires which can be selectively adjusted as required to cause the teeth to assume the most orthodontically desirable positions. Such positions can also be achieved by the application of bonded brackets or removable devices well known to those skilled in the orthodontic art. These positions are determined with respect to such considerations as proper occlusion and aesthetic appearance. Once the teeth are correctly positioned, a period of time is required during which the teeth must be maintained in their correct positions to stabilize them and allow them to reach a state of equilibrium with the forces exerted on the teeth by the tongue, the perioral and intraoral muscles, recalcification of the bone and reorganization of the many fibers between tooth and bone and between tooth and tooth. In addition, the settling of the teeth into proper occlusal relationships influences the time required to reach the required equilibrium. This time period can vary considerably, depending upon whether the repair of bone, periodontal structures or gingival attachments had to be achieved to produce the desired tooth movement. The stabilizing function is typically performed by the application of a second orthodontic appliance known as a retainer. Previously, the sequential application of these two separate orthodontic appliances has been required to provide a complete course of orthodontic treatment for most orthodontic patients.

The available retainer-like orthodontic appliances are intended to be employed solely for retaining the teeth in previously achieved orthodontically correct positions. A retainer-like orthodontic appliance has not heretofore been disclosed which can perform both the conventional retention function just described and the repositioning functions normally performed by other orthodontic appliances. In addition, the known orthodontic retainers are characterized by certain disadvantages which interfere with the optimum performance of their retention function. For example, a commonly employed design of orthodontic retainer includes a hard plastic overlay molded to conform to the contours of the patient's hard palate and fit securely against the lingual surfaces of the teeth which supports a single strand of wire extending horizontally across the labial surface of the anterior teeth. The retainer wire must be fitted to each individual patient and usually extends from the interproximal of the cuspid and first bicuspid to the interproximal of the opposite cuspid and first bicuspid, although the wire may extend around all of the teeth. The tension of the wire and, thus, the pressure exerted by the wire to maintain the teeth in their correct positions is adjusted by varying the distance between the vertical legs of a pair of opposed, inverted U-shaped adjustment loops. A retainer wire of this design is difficult to adjust so that the optimum amount of pressure is applied to the teeth. Another type of available retainer which is also difficult to adjust provides a wire with plastic poured over it so that it conforms exactly to the teeth to be retained.

The orthodontic retainer disclosed in U.S. Pat. No. 3,994,068 to Robert A. Goshgarian includes an improved adjustment loop configuration which reduces the retainer wire adjustment problem to a great extent. However, as is the case with other prior art retainers, the function of this retainer is limited to maintaining the teeth in the optimum positions achieved by the prior application of other orthodontic appliances. Neither the retainer disclosed in U.S. Pat. No. 3,994,068 nor other known prior art retainers is capable of performing both the positioning functions typically performed by other orthodontic appliances and the retention functions performed by conventional retainers.

DISCLOSURE OF THE INVENTION

It is, therefore, a primary object of the present invention to provide a retainer-like orthodontic appliance including a palatal overlay for supporting on the labial side of the teeth a pair of dual function opposed cross over retainer wires which may be easily positioned and adjusted in a manner to cause the movement of one or more teeth to achieve desired orthodontically correct positions or to maintain the teeth in the positions achieved by the prior application of other orthodontic appliances.

It is another object of the present invention to provide a retainer-like orthodontic appliance including a pair of opposed cross over labial retainer wires which may be adjusted to cause a selected tooth to move in one of several different directions.

It is still another object of the present invention to provide a retainer-like orthodontic appliance including a pair of opposed cross over labial retainer wires to which may be attached auxiliary wires to facilitate the movement of selected teeth in a multiplicity of desired orientations.

It is a further object of the present invention to provide a retainer-like orthodontic appliance including a gingival overlay molded to conform to the periodontal structures on the lingual side of the lower teeth for supporting a pair of opposed cross over labial retainer wires which may be adjusted to move selected teeth in desired directions or to retain the teeth in previously achieved positions.

It is an additional object of the present invention to provide an orthodontic retainer having a pair of opposed cross over retainer wires which are easily fit to the individual patient and readily adjusted to apply pressure as needed to maintain the teeth in the positions achieved by prior orthodontic treatment.

It is yet another object of the present invention to provide an orthodontic retainer including a palatal overlay for supporting on the labial side of the teeth a single retainer wire having a centrally positioned inverted U-shaped loop adjustable to maintain teeth in the position achieved by prior orthodontic treatment. The single wire retainer can be converted to a double wire retainer by clipping the wire in the loop portion and straightening the wire sections to form a pair of opposing cross over wires which can be adjusted to position the teeth as well as maintain them in a position achieved by previous treatment.

Further objects and advantages will become apparent from the following description and claims and from the accompanying drawings.

In accordance with the aforesaid objects an orthodontic appliance is provided including a palatal overlay molded to conform to the shape of the anterior portion of the patient's hard palate and to fit securely against the gingival edge of the lingual surface of the teeth contacted by the palatal overlay. A pair of opposed spaced retaining and positioning wires are inserted in the palatal overlay and secured therein to exit the lingual edge of the overlay in the interproximal of the cuspid and first bicuspid to lie on the labial side of the teeth. The free ends of the wires are bent toward the midline so that one wire is gingival or incisal to the other, and the wires cross over for a distance necessary to achieve the desired positioning and/or retaining effect. Clasps may be inserted in the posterior portion of the palatal overlay to assure that the retainer is securely anchored in the mouth. An orthodontic appliance for positioning or retaining the lower teeth is also provided including a gingival overlay molded to conform to the lingual side of the patient's lower gums and adjacent periodontal structures and to fit securely against the lingual surface of the bottom teeth. The gingival overlay supports a pair of opposed spaced retainer wires secured in the overlay and positioned to exit the overlay in the interproximal of the cuspid and the first bicuspid. The free ends of the wires are bent toward the midline so that one wire is gingival or incisal to the other and the wires cross over for a distance necessary to achieve the desired positioning and/or retaining effects. An additional embodiment is provided including a palatal ovelay for supporting on the labial side of the teeth a single continuous retainer wire having a central vertical adjustment loop for performing primarily a retaining function. If it is desired in addition to use this retainer to position the teeth, the central loop may be clipped and the free ends of the wire straightened to form the pair of opposed cross over wires of the preferred embodiment.

BRIEF DESCRIPTION OF THE DRAWINGS

FIG. 1 is a perspective view of the orthodontic appliance of the present invention including a palatal overlay for use in treating the upper teeth;

FIG. 2 is a front elevational view diagramatically illustrating the appliance of FIG. 1 in place around the upper teeth of a patient;

FIG. 3 is a bottom plan view of the roof of the mouth showing the palate, the dental arch and the appliance of FIG. 1 in place;

FIG. 4 is a perspective view of the orthodontic appliance of the present invention including a gingival overlay for use in treating the lower teeth;

FIG. 5 is a perspective view of a second embodiment of the orthodontic appliance of the present invention including a palatal overlay for use in treating the upper teeth;

FIG. 6 is a front elevational view diagramatically illustrating the appliance of FIG. 5 in place around the upper teeth of a patient;

FIG. 7 illustrates a modification which may be made to the appliance of FIG. 5;

BEST MODE FOR CARRYING OUT THE INVENTION

Figure 8:
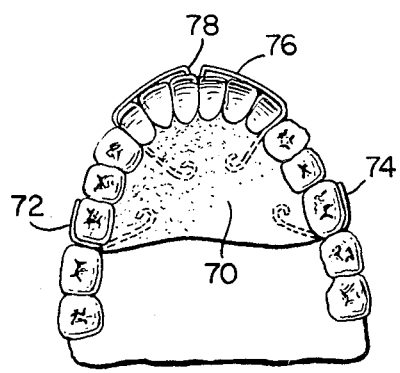
FIG. 8 is a bottom plan view of the roof of the mouth showing the palate, the dental arch and the appliance of FIGS. 5-7 in place.

Referring now to the drawings, FIGS. 1, 2 and 3 illustrate the preferred embodiment of the orthodontic appliance of the present invention in a form suitable for use in treating an orthodontic patient's upper teeth. The appliance, which generally resembles a retainer known as a Hawley-type retainer, includes a palatal overlay 2 which supports a pair of posteriorly placed opposed clasps 6 and 8, and a pair of opposed anteriorly placed cross over retaining and positioning wires 10 and 12. The palatal overlay is formed of commercially available materials, generally a suitable plastic, according to conventionally used techniques to fit a patient's upper jaw and palate. In many cases, the orthodontist will have constructed a model of the patient's jaw and palate which can be utilized in forming the palatal overlay. To achieve the desired treatment results, the palatal overlay portion of the appliance must conform as precisely as possible to the shape of the patient's palate and fit securely against the lingual surfaces of the upper teeth. This causes the edges of the overlay to assume a scalloped appearance, with the points 14 fitting closely to the interproximals of two adjacent teeth, and the curved portion 16 conforming to the contour of the lingual surface at about the gum line of the tooth central to points 14.

While the overlay is in a suitably malleable state, one end of each of the clasps 6 and 8 is bent to form a hook and imbedded in the posterior portion of the ovelay as indicated by the dashed outline 18 of the imbedded portion of clasp 6 and the dashed outline 20 of the imbedded portion of clasp 8. The purpose of forming a hook in the end of the clasp which is embedded in the overlay is to provide a firm attachment between the wire and the plastic so that the wire will not pull out of the plastic. Other shapes besides the hook shape shown, such as a right angle bend and a circular bend (not shown), will provide the same anchoring function. The free ends of clasp 6 and 8 are then shaped to fit around the teeth, usually the first molars, adjacent to the posterior portion of overlay 2. The clasps shown herein are generally referred to as "C" molar clasps and function to anchor the retainer in the mouth. Other types of clasps known to those skilled in the orthodontic art, such as Adams clasps, ball end clasps, butterfly clasps or any of the many known clasps may be used for the same purpose.

Retaining and positioning wires 10 and 12 are also imbedded in palatal overlay 2 while the overlay is in a suitably malleable state. A portion 22 of wire 10 is bent to form a hook as shown, or one of the other shapes discussed above, on the end and imbedded in the overlay, while a portion 24 of wire 12 is bent in the same manner and imbedded on the opposite side of the overlay. Clasps 6 and 8 and retaining and positioning wires 10 and 12 are formed of an appropriate filamentous, resiliently flexible material having a round cross-sectional configuration, such as, for example, stainless steel.

The retaining and positioning wires are preferably positioned so that the free ends exit the overlay at the interproximals of the cuspids and the adjacent bicuspids. However, it may be more advantageous to position wires 10 and 12 differently, depending upon the type of treatment indicated. When wire 10 is positioned in overlay 2 in the preferred position, it moves over the interproximal of the cuspid and the first bicuspid to the labial side of the teeth. The free end of wire 10 is bent toward the midline of the dental arch and at about the interproximal of the cuspid and the maxillary lateral incisor is offset slightly in a lingual direction (not shown) to conform to the orientation of the labial surface of the maxillary lateral incisor, which in a perfect dentition is positioned slightly back in relation to the adjacent cuspid and central incisor. An additional slight bend in a labial direction is included in wire 10 (not shown) at about the interproximal of the maxillary lateral incisor and central incisor to cause it to contact the central incisor. The free end of wire 10 then extends for a distance beyond the midline of the dental arch to end preferably at about the distal side of the opposite central incisor. The free end of wire 10 may extend to the distal sides of any of the teeth on the side of the dental arch opposite the origin or wire 10 beyond the central incisor if it is desired to exert pressure on any of these teeth, such as to move a labially displaced tooth into position. The free end of wire 12 follows essentially the same contours as wire 10, originating in the interproximal of the cuspid and bicuspid on the opposite side of the dental arch from retainer wire 10 and terminating at about the distal side of the central incisor opposite its origin.

FIG. 2 illustrates the upper dental arch with the orthodontic appliance of FIG. 1 in place as it appears when viewed from the front of the mouth. The free end of wire 10 originates on the labial side of the teeth in the interproximal 25 of the first bicuspid 26 and the cuspid or canine 28 and is bent toward the midline of the dental arch, causing wire 10 to cross over maxillary lateral incisor 30, left central incisor 32, and right central incisor 34, terminating at the distal side 35 of right central incisor 34 on the opposite side of the midline from the origin of wire 10. The free end of wire 12 originates on the labial side of the teeth in the interproximal 36 of the first bicuspid 38 and cuspid or canine 40 and is bent toward the midline of the dental arch, causing retainer wire 12 to cross over maxillary lateral incisor 42, right central incisor 34 and left central incisor 32, terminating at the distal side 44 of left central incisor 32 on the opposite side of the midline from the origin of wire 12. FIG. 2 illustrates, in addition, the placement of clasp 6 on the labial surface of left first molar 44 and clasp 8 on the opposite right first molar 46. Left second bicuspid 48 and right second bicuspid 50, shown in FIG. 2 as not contacted by either wire 10 or wire 12, may in some cases be contacted by either or both of the wires, depending upon whether either or both of these teeth require positioning to achieve a more desirable orientation. Depending upon the course of orthodontic treatment to be pursued, cross over wires 10 and 12 can be joined together either by soldering or by use of a sleeve over the area of overlap, such as from 35 to 44 as shown in FIG. 2, to convert the orthodontic retainer of the present invention into a single wire retainer.

In FIG. 3, the orthodontic appliance of the present invention is shown applied to the upper teeth as it would appear when looking toward the roof of the patient's mouth. The contours of palatal overlay 2 which permit the overlay to fit securely against the lingual side of the upper teeth can be clearly seen. The palatal overlay will generally terminate at a depth approximating the distance between the central incisors and a line drawn across the hard palate between the distal sides of the first molars. If second molars 52 and 54 or third molars 56 and 58 require treatment, this may be achieved by the attachment to palatal overlay 2 of additional wires (not shown) which extend to the labial side of the teeth and are bent in a lingual direction to contact these molars.

FIG. 4 illustrates the orthodontic appliance of the present invention adapted for application to the lower teeth of a patient for whom orthodontic treatment of these teeth is indicated. The appliance includes a gingival overlay 60 molded to conform to the periodontal structures on the lingual side of the lower jaw and shaped to fit securely against the gingival edge of the lingual surface of the lower teeth. The appliance further includes a pair of opposed clasps 62 and 64 imbedded in the plastic material of the gingival overlay in the same manner clasps 6 and 8 are imbedded in palatal overlay 2 as described above. Clasps 62 and 64 are preferably positioned so that the free ends cross to the labial side of the teeth in the interproximal of the first and second bicuspids, although other positions may be utilized if more advantageous to a particular patient. Retaining and positioning wires 66 and 68 correspond to retaining and positioning wires 10 and 12 described above and are preferably positioned in gingival overlay 60 so that the free ends cross to the labial side of the lower teeth in the interproximal of the lower cuspids and lower first bicuspids. Retainer wire 66 is shown anterior to wire 68, with the area of cross over preferably across the two central incisors. The extent of the cross over may be varied as required to apply pressure to teeth other than the central incisors.

FIGS. 5 through 7 illustrate another embodiment of the orthodontic appliance of the present invention. This embodiment also includes a palatal overlay supporting clasps in a manner similar to the embodiment illustrated in FIGS. 1 through 3. However, this embodiment includes a different retainer wire configuration from that of the preferred embodiment. FIG. 5 illustrates a perspective view of the appliance, which includes a palatal overlay 70. As described above in conjunction with FIGS. 1 through 3, the palatal overlay of this embodiment is molded of a suitable plastic material to conform to the contours of the orthodontic patient's hard palate and fit securely against the lingual surfaces of the teeth it contacts. Clasps 72 and 74 are positioned and then imbedded in overlay 70 to cross to the labial side of the teeth in the interproximal of the first and second molars, although the position of these clasps can be varied if desired. The single retainer wire 76 of this embodiment is imbedded in the plastic of palatal overlay 70 and preferably positioned to cross the labial side of the teeth in the interproximal of the cuspid and the first bicuspid, thus exerting its stabilizing effect on the six anterior teeth. The precise position of the single retainer wire 76 can be varied from the preferred position as indicated in the treatment of individual patients. Single retainer wire 76 differs from prior art single retainer wires in several significant aspects. Wire 76 is a continuous, substantially horizontal bar in which a single inverted U-shaped adjustment loop 78 has been formed. Adjustment loop 78 is shown in FIGS. 5 and 6 as being positioned essentially in the center of wire 76 and located at about the midline of the dental arch where it contacts the interproximal of the two central incisors. However, it is contemplated to be within the scope of the present invention to position loop 78 in other locations along wire 76 as well as to provide additional loops in the wire as needed. In addition, although wire 76 is shown in FIGS. 5 through 7 as extending across the six anterior teeth, from one cuspid to the opposite cuspid, if required to achieve the required stability, wire 76 could extend across any number of teeth from one to the complete dental arch. Placement of the inverted loop wire at any location in the upper or lower dental arch, as well as the simultaneous application of two or more such loops to different parts of the dental arch, are also contemplated to be within the scope of the present invention. Activation of the adjustment loop 78, for example, by moving the vertical sides 79a and 79b of the loop closer together, can be accomplished to move teeth closer together or in a lingual direction. Although the primary function of this embodiment of the orthodontic appliance of the present invention is to retain or stabilize the teeth in positions achieved by prior orthodontic treatment, the configuration of wire 76 can be modified to produce the double wire configuration of the preferred embodiment. Such a modification allows this embodiment of the orthodontic appliance of the present invention to be applied either to position the teeth or to maintain them in previously achieved positions, as shown in FIG. 7, in the same manner as the preferred embodiment. This is achieved simply by cutting loop 78 in the center to divide wire 76 into two approximately equal lengths, 76a and 76b, having free ends 80 and 82, respectively. The curved portions of wires 76a and 76b are then straightened so that free end 80 of wire 76a overlaps wire 76b and free end 82 of wire 76b overlaps wire 76a. The orthodontic appliance thus can be modified to assume the double wire configuration of the preferred embodiment and is capable of performing the dual retaining or stabilizing and positioning functions that can be performed by that structure. The unmodified single wire, single vertical adjustment loop configuration just described is particularly useful in maintaining the teeth in their treated positions after first stage mixed or primary dentition treatment. Conversion from the single wire to the double wire configuration will most likely be desired in cases in which the appliance was not worn by the patient as prescribed and the teeth resumed their pretreatment positions, thus necessitating their repositioning.

FIG. 8 illustrates this embodiment of the present invention as it would appear when viewed from the bottom of the mouth. The way in which loop 78 contacts the teeth can be clearly seen in this view.

The arrangement of the pair of opposed cross over retaining and positioning wires described above allows the orthodontist a wide latitude of treatment options. The double wire configuration permits the orthodontic appliance of the present invention to perform a dual function. This appliance can be used like a conventional retainer in a patient whose teeth have been moved into orthodontically correct positions by the prior application of other orthodontic appliances and must be retained in these positions until the newly positioned teeth and their periodontal structures attain a state of equilibrium and the appliance is no longer needed. In addition, the orthodontic appliance of the present invention may be efficaciously applied to a patient whose teeth are not in their optimum positions and must be moved to achieve the most desirable orthodontically correct orientations. Moreover, the appliance possesses the added versatility of permitting one of the wires to be utilized to stabilize selected teeth in previously achieved positions and the other to be applied to one or more teeth which must be moved.

Figure 9:
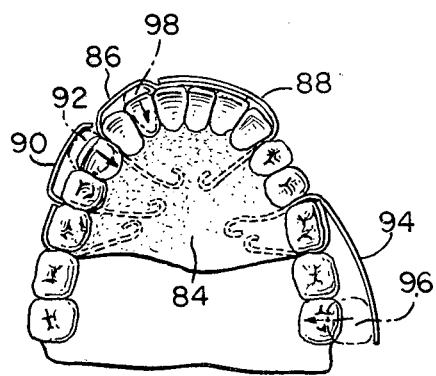
FIG. 9 is a bottom plan view of the roof of the mouth showing the palate, the dental arch and the appliance of FIG. 1 with modifications in place.

The basic double wire arrangement of the orthodontic appliance of the present invention can be modified to enable its application to teeth which require movement in any one of the seven directions in which teeth customarily must be moved. Utilization of the unique double wire arrangement which has been appropriately modified or not as dictated by the direction in which movement is desired permits movement of a tooth in a mesial, distal, labial or lingual direction. In addition, teeth may be intruded, extruded or rotated, as required. Without the use of additional wires, the two cross over wires can both be bent to clasp a selected tooth to rotate it or move it in a lingual direction. Additional wires may also be attached either to the palatal or gingival overlay material or to the double wires to cause pressure to be exerted on a selected tooth, as shown in FIG. 9. For example, if pressure is required to be applied to a tooth on the same side of the midline as the origin of wire 86, which corresponds to wire 10 in FIGS. 1-3, an additional wire 90 positioned substantially parallel to wire 86 can be added to the appliance. This wire will cause the lingual movement of bicuspid 92 from the incorrect position shown in dashed lines to the correct position shown in solid lines. If required, a similarly positioned wire (not shown) could be added to apply pressure to the same side of the midline as the origin of wire 88 which corresponds to wire 12 in FIGS. 1-3. If movement of a second or third molar in a lingual direction must be accomplished, a positioning wire 94 can be imbedded in the palatal overlay, moved to the labial side of the teeth at about the interproximal of the bicuspids (not shown) or the interproximal of the second bicuspid and first molar, as indicated, and bent distally to contact the molar to be treated, such as molar 96 in FIG. 9. This same wire can be modified to hold or intrude a tooth simply by bending the wire to result in a horizontal lingual bend over the occlusal of the tooth to be intruded. Wire 86, as shown in FIG. 9, does not contact the anterior teeth until it contacts lateral incisor 98 to move it lingually. After movement into the correct position (from that shown in dashed lines to that shown in solid lines) is achieved, wire 88 can be used as a regular retainer wire. Wire 86 can then be quickly readapted to perform a labial retainer wire function.

Figure 10:
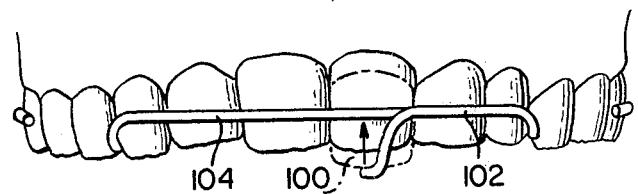
FIG. 10 is a front elevational view diagrammatically illustrating the appliance of FIG. 1 including an incisal bend for causing the intrusion of a selected tooth.

Additional auxiliary wires can be soldered or attached in like manner to wires 10 and 12 (FIGS. 1-3) to cause the movement of particular teeth mesially or distally as required to achieve optimum orientation or to move a particular tooth into an existing space. If intrusion or rotation of a tooth must be accomplished, wires (not shown) positioned vertically with respect to the dual function cross over wires can be soldered to the cross over wires to intrude or rotate the tooth as needed. Alternatively, as shown in FIG. 10, the cross over wires themselves may be bent incisally to intrude a tooth, such as central incisor 100. Cross over wire 102 includes an incisal bend which causes incisor 100 to be intruded into the correct position shown by the solid lines. Wire 104 is maintained in a substantially horizontal position. Such an incisal bend can be positioned in any location on the dental arch to intrude any tooth.

If spaces between the teeth must be closed by moving the adjacent teeth closer together, the cross over wires will support hooks to receive elastic bands which cause the teeth to move closer together and close the spaces. Once the teeth have been moved and the spaces closed, the hooks can be removed and wire 10 or wire 12 (FIGS. 1–3) can then be applied as a retainer to the labial surface of the teeth to stabilize them in their newly achieved positions. Alternatively, the cross over wires can be cut and bent to form hooks (not shown) to support a piece of elastic stretched across the anterior teeth.

The attachment of the additional and auxiliary wires to the cross over wires as described above achieves movement of the teeth through the application of pressure to the labial surface of the teeth. Pressure can also be applied to the lingual surface of the teeth to cause movement of a selected tooth or teeth in a mesial, distal or labial direction by means of a pair of opposed overlapping lingual wires supported by the plastic material of the palatal or gingival overlay on the lingual side of the teeth which are similarly positioned in the overlay and correspond to the configurations of labial wires 10 and 12 (FIGS. 1–3).

INDUSTRIAL APPLICABILITY

The orthodontic appliance of the present invention will find broad application to many types of orthodontic problems for which treatment is indicated. Teeth may be moved causing them to occupy their most desirable positions in the mouth by the utilization of the appliance of the present invention and the modifying structures which may be added thereto. In addition, once the teeth have been optimally positioned, the appliance of the present invention may be worn by an orthodontic patient to maintain the teeth in their orthodontically correct positions until the required stability has been achieved.

I claim:

1. An orthodontic appliance for application to the teeth of a patient in whom orthodontic treatment is indicated, said orthodontic appliance comprising:
   (a) support means molded to conform to the contours of the periodontal mouth structures adjacent the lingual side of the teeth and to fit securely against the gingival edges of the lingual surface of the teeth for mounting positioning wires and clasps;
   (b) a pair of dual function positioning and retaining means for contacting the labial surfaces of the teeth and moving the teeth to a desired orientation or maintaining teeth in a previously achieved desired orientation, each one of said pair of dual function positioning and retaining means having a secured end and a free, unsecured end, the free end of one of said positioning and retaining means being adapted to extend across the anterior teeth from the cuspid on one side of the mouth to at least the opposite maxillary lateral incisor, and the free end of the other of said positioning and retaining means being adapted to extend across the anterior teeth from the opposite cuspid to at least the opposite maxillary lateral incisor; and
   (c) anchor means connected to said support means for securing said orthodontic appliance to the posterior teeth.

2. The orthodontic appliance described in claim 1, wherein said support means comprises a palatal overlay molded to conform substantially to the contours of the patient's hard palate and to the contours of the gingival edge of the lingual surface of the upper teeth, causing said overlay to fit securely over the hard palate and against the lingual surface of the upper teeth.

3. The orthodontic appliance described in claim 2, wherein said pair of dual function positioning and retaining means comprises a pair of opposed spaced substantially horizontal wires, each of said wires having a secured end and a free end, wherein said secured end of each of said wires is imbedded in said support means and said free end of each of said opposed wires is positioned to exit said support means at substantially the interproximal of the cuspid and the adjacent bicuspid and is bent toward the middle of said support means, causing the free end of one of said opposed wires to be positioned anteriorly and cross over the free end of the other of said opposed wires for a predetermined distance beyond the midline of said support means.

4. The orthodontic appliance described in claim 3, wherein each of said opposed wires includes in the area of the interproximal of the cuspid and the lateral incisor a portion slightly offset in a lingual direction relative to adjacent portions.

5. The orthodontic appliance described in claim 4, wherein each of said opposed wires further includes in the area of the interproximal of the maxillary lateral incisor and the central incisor a portion bent in a labial direction causing each of said opposed wires to contact its subjacent central incisor.

6. The orthodontic appliance described in claim 5, wherein the free end of each of said opposed wires extends across the midline of the dental arch and terminates at the distal side of the central incisor opposite the secured end of each of said opposed wires.

7. The orthodontic appliance described in claim 3, wherein the free end of said anteriorly positioned wire extends beyond the midline of the dental arch and terminates at the distal side of the lateral incisor opposite the secured end of said wire.

8. The orthodontic appliance described in claim 6 wherein said palatal overlay includes a third wire imbedded in said overlay and positioned to cross to the labial side of the teeth on the same side of the midline of the dental arch as one of said pair of opposed spaced substantially horizontal wires.

9. The orthodontic appliance described in claim 6, wherein said pair of opposed spaced substantially horizontal wires includes attached thereto auxiliary wires for contacting and exerting pressure on selected teeth.

10. The orthodontic appliance described in claim 1, wherein said support means comprises a gingival overlay molded to conform to the contours of the periodontal structures on the lingual side of the lower teeth and to the contours of the gingival edge of the lingual surface of the lower teeth.

11. The orthodontic appliance described in claim 10, wherein said pair of dual function positioning and retaining means comprises a pair of opposed spaced substantially horizontal wires, each of said wires having a secured end and a free end, wherein said secured end is imbedded in said support means and said free end of each of said opposed wires is positioned to exit said support means at the interproximal of the cuspid and the adjacent bicuspid and is bent toward the middle of said support means, causing the free end of one of said opposed wires to be positioned anteriorly and cross over the free end of the other of said opposed wires for a predetermined distance beyond the midline of said support means.

12. The orthodontic appliance described in claim 11, wherein each of said opposed wires further includes in about the area of the interproximal of the cuspid and the lateral incisor a portion slightly offset in a lingual direction relative to adjacent portions.

13. The orthodontic appliance described in claim 12, wherein each of said opposed wires further includes in about the area of the interproximal of the maxillary lateral incisor and the central incisor a portion bent in a labial direction causing each of said opposed wires to contact its subjacent central incisor.

14. The orthodontic appliance described in claim 13, wherein the free end of each of said opposed wires extends across the midline of the dental arch and terminates at the distal side of the central incisor opposite the secured end of each of said opposed wires.

15. An orthodontic appliance for application to the teeth of a patient in whom orthodontic treatment is desired, wherein said orthodontic appliance can be converted from an orthodontic retainer for maintaining the teeth in positions achieved by the prior application of other appliances to a positioning appliance for moving the teeth into orthodontically correct positions, said orthodontic appliance comprising:

(a) support means molded to conform to the contours of the periodontal mouth structures adjacent the lingual side of the teeth and to fit securely against the gingival edges of the lingual surface of the teeth for mounting positioning wires and clasps;

(b) retaining means for contacting the labial surfaces of the anterior teeth and stabilizing the teeth in orthodontically desirable positions, said retaining means comprising a single continuous substantially horizontal wire including a centrally positioned open vertical loop for adjusting the tension of said wire; and (c) another means connected to said support means for securing said orthodontic appliance to the posterior teeth.

16. The orthodontic appliance described in claim 15, wherein said open vertical loop is of sufficient depth to permit the free end of one wire to overlap the free end of the second wire when said single horizontal wire is severed at a point substantially in the center of said loop and straightened to form a pair of wires.

17. The orthodontic appliance described in claim 8, wherein said palatal overlay includes a fourth wire imbedded in said overlay and positioned to cross to the labial side of the teeth on the same side of the midline of the dental arch as one of said pair of opposed space substantially horizontal wires, said fourth wire being adapted to extend in a direction opposite that of said one of said pair of opposed spaces wires so that said fourth wire contacts teeth posterior to those contacted by said one of said opposed spaced substantially horizontal wires.

18. An orthodontic appliance for application to the teeth of a patient in whom orthodontic treatment is indicated, said orthodontic appliance comprising:

(a) support means molded to conform to the contours of the periodontal mouth structures adjacent the lingual side of the teeth for mounting positioning wires and clasps;

(b) a pair of elongated opposed, dual function positioning and retaining means for contacting the surfaces of the teeth and moving the teeth to a desired orientation or maintaining the teeth in a previously achieved desired orientation, each one of said pair of positioning and retaining means having a secured end and a free, unsecured end, said free end of each of said positioning and retaining means extending across the teeth toward the secured end of the opposite one of said positioning and retaining means, the free end of one of said positioning and retaining means crossing over the free end of the other of said positioning and retaining means across the surface of at least one tooth, and (c) anchor means connected to said support means for securing said orthodontic appliance to the teeth.

* * * * *